US00PP20788P2

(12) United States Plant Patent
Hanes

(10) Patent No.: US PP20,788 P2
(45) Date of Patent: Feb. 23, 2010

(54) *VERBENA* PLANT NAMED 'LAN DAREDA'

(50) Latin Name: *Verbena hybrida*
Varietal Denomination: Lan Dareda

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,178

(22) Filed: Dec. 10, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para
(74) *Attorney, Agent, or Firm*—S. Matthew Edwards

(57) ABSTRACT

A new *Verbena* plant named 'Lan Dareda,' particularly distinguished by dark red-colored large flowers with vigorous and free-branching, mounding and outwardly spreading growth habit, medium yellow-green foliage and an exceptional tolerance to powdery mildew.

1 Drawing Sheet

Latin name of the genus and species of the plant claimed: *Verbena hybrida.*

Varietal denomination: 'Lan Dareda'.

BACKGROUND OF THE NEW PLANT

The present invention comprises a new *Verbena*, botanically known as *Verbena hybrida*, and hereinafter referred to by the variety name 'Lan Dareda.'

'Lan Dareda' is a product of a planned breeding program. The new cultivar 'Lan Dareda' has dark red-colored large flowers with vigorous and free-branching, mounding and outwardly spreading growth habit, medium yellow-green foliage and an exceptional tolerance to powdery mildew.

'Lan Dareda' originated from a hybridization in a controlled breeding program in Gilroy, Calif. USA. The female parent was an unpatented hybrid seedling identified as '04-1801-3' with red color. '04-1801-3' has lighter red colored flowers, larger foliage, and a little more compact plant habit 'Lan Dareda.'

The male parent of 'Lan Dareda' was a patented commercial variety identified as 'Aztec Velvet Red' (U.S. Plant Pat. No. 16,667). 'Aztec Velvet Red' has smaller flower size, shorter and lighter green peduncles, and smaller foliage size than 'Lan Dareda.'

'Lan Dareda' was selected as one flowering plant within the progeny of the stated cross in May 2005 in a controlled environment in Gilroy, Calif. USA. The pollination took place in May 2004 and the seed sown in March 2005.

The first act of asexual reproduction of 'Lan Dareda' was accomplished when vegetative cuttings were taken from the initial selection in the May 2005 in a controlled environment in Gilroy, Calif. USA.

Horticultural examination of plants grown from cuttings of the plant initiated in May 2005 in Gilroy, Calif. USA, and continuing thereafter, has demonstrated that the combination of characteristics as herein disclosed for 'Lan Dareda' are firmly fixed and are retained through successive generations of asexual reproduction.

'Lan Dareda' has not been observed under all possible environmental conditions. The phenotype may vary significantly with variations in environment such as temperature, light intensity and day length.

A Plant Breeder's Right for this cultivar was applied for in Canada on Dec. 24, 2007. 'Lan Dareda' has not been made publicly available more than one year prior to the filing of this application.

DESCRIPTION OF THE DRAWINGS

The accompanying photographic drawing shows typical flower and foliage characteristics of 'Lan Dareda' with colors being as true as possible with an illustration of this type. The photographic drawing shows 3 flowering potted plants of the new variety in a 14 inch container, and a close-up of the flowers. These plants were grown and photographed in Gilroy, Calif. USA in the summer of 2007.

DETAILED BOTANICAL DESCRIPTION

The measurements were taken on plants growing in Gilroy, Calif. USA in March 2008. The plants were growing in 4 inch plastic pots in a greenhouse trial. These plants were about 3 months old. Color Chart used: Royal Horticultural Society Colour Chart (R.H.S.) 2001

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this *Verbena* as a new and distinct variety.

TABLE 1

DIFFERENCES BETWEEN THE NEW CULTIVAR 'LAN DAREDA' AND A SIMILAR VARIETY

| | 'Lan Dareda' | 'Balazreve' (U.S. Plant Pat. No. 16,667) |
|---|---|---|
| Flower size | Little larger | Little smaller |
| Peduncle size/color | Longer/medium green | Shorter/lighter green |
| Foliage size | Larger | Smaller |

Plant:
- *Form, growth and habit.*—Mounding and outwardly spreading growth habit; vigorous and free-branching.
- *Plant height.*—14–16 cm.
- *Plant width.*—45–48 cm.

Foliage:
- *Arrangement.*—Opposite, simple.
- *Immature, leaf color, upper surface.*—Closest to RHS 146A but a little greener.
- *Lower surface.*—RHS 137C.
- *Mature, leaf color, upper surface.*—RHS 147A.
- *Lower surface.*—RHS 137C.
- *Length.*—4.5–5.5 cm.
- *Width.*—3.4–3.6 cm.
- *Shape.*—Ovate.
- *Base shape.*—Truncate.
- *Apex shape.*—Acute.
- *Margin.*—Serrulate and slightly irregularly incised.
- *Texture, upper surface.*—Hirsute.
- *Texture, lower surface.*—Hirsute on veins only.
- *Color of veins, upper surface.*—RHS 144B basally; otherwise indistinct.
- *Color of veins, lower surface.*—RHS 144B basally; otherwise indistinct.
- *Petioles color.*—RHS 144B.
- *Petioles length.*—0.9–1.1 cm.
- *Diameter of petiole.*—0.2 cm.
- *Texture.*—Hirsute; glandular hairs.

Stem:
- *Quantity of main branches per plant.*—6–8.
- *Quantity of leaves per lateral branch.*—10–12.
- *Color of stem.*—RHS 146A but a little lighter; with the young stems having a hint of anthocyanins of about RHS 166A.
- *Length of stem.*—18–22 cm.
- *Diameter.*—0.3 cm.
- *Length of internodes.*—2.5–4.0 cm.
- *Texture.*—Hirsute; pilose.

Inflorescence:
- *Type.*—Terminal raceme.
- *Blooming habit.*—Flowers continuously from spring through fall.
- *Lastingness of individual blooms on the plant.*—5–7 days in the greenhouse.
- *Fragrance.*—None.
- *Number of inflorescences per plant.*—15–22 at various stages.
- *Color of peduncle.*—Between RHS 146A and B.
- *Length of peduncle.*—5.5–8.0 cm.
- *Peduncle diameter.*—0.2 cm.
- *Texture.*—Hirsute; pilose; glandular hairs, many of about RHS 53A.
- *Horizontal diameter of inflorescence.*—5.5–6.0 cm.
- *Depth of inflorescence.*—4.0–5.0 cm.
- *Number of florets per inflorescence (including any buds at the time).*—28–34.

Bud (just before opening):
- *Color.*—RHS 46A but a little darker.
- *Length.*—1.8–2.2 cm.
- *Width.*—0.3–0.4 cm.
- *Shape.*—Tubular.

Corolla:
- *Form.*—Sessile; Salverform, composed of 5 petals.
- *Immature color, upper surface.*—Darker than RHS 46B appearing more velvety.
- *Lower surface.*—Between RHS 53C and D with RHS 155B basally.
- *Mature color, upper surface.*—RHS 46B fading to lighter than RHS 46B.
- *Lower surface.*—Between RHS 53C and D with RHS 155B basally.
- *Floret diameter.*—2.6–2.8 cm.
- *Length of petal.*—1.1–1.3 cm.
- *Width of petal.*—1.0–1.4 cm.
- *Petal shape.*—Obovate.
- *Apex shape.*—Emarginate to cleft.
- *Margin.*—Entire.
- *Petal texture, upper surface.*—Papillose.
- *Lower surface.*—Few hirsute; few glandular hairs.
- *Corolla tube length.*—1.7–1.9 cm.
- *Corolla tube color inside.*—RHS 155B.
- *Tube color outside.*—RHS 155B.
- *Corolla textura, inside.*—Glabrous.
- *Outside.*—Glabrous basally; glandular hairs at the flare.

Calyx:
- *Type.*—Five sepals whose margins are fused to each other along their length, with a transparent membrane of less than 0.1 cm in width and with one smaller sepal attached to the base of the calyx.
- *Color of sepals.*—RHS 143A.
- *Length of sepals.*—1.2–1.4 cm.
- *Width of sepals.*—0.1 cm.
- *Sepal shape.*—Linear.
- *Apex shape.*—Acute.
- *Margins.*—Entire.
- *Texture.*—Heavily hirsute; glandular hairs basally of about RHS 53A.

Reproductive organs:
- *Pistil.*—1.
- *Length.*—1.7 cm.
- *Style color.*—RHS 145B.
- *Style length.*—1.4–1.6 cm.
- *Stigma color.*—RHS 144A.
- *Stamens.*—Anthers and filaments fused to upper half of corolla tube; four anthers with two pollen sacs per anther.
- *Length filaments.*—0.1–0.2 cm.
- *Color of filaments.*—RHS 145B.
- *Length of anthers.*—0.1 cm.
- *Anther color.*—RHS 145B.
- *Color of pollen.*—RHS 2C.
- *Pollen amount.*—Scarce.
- *Fertility/seed set.*—Not observed on this hybrid.

Disease/pest resistance: Disease resistance or susceptibility has not been observed on this hybrid.

What is claimed is:

1. A new and distinct variety of *Verbena* plant named 'Lan Dareda,' substantially as illustrated and described herein.

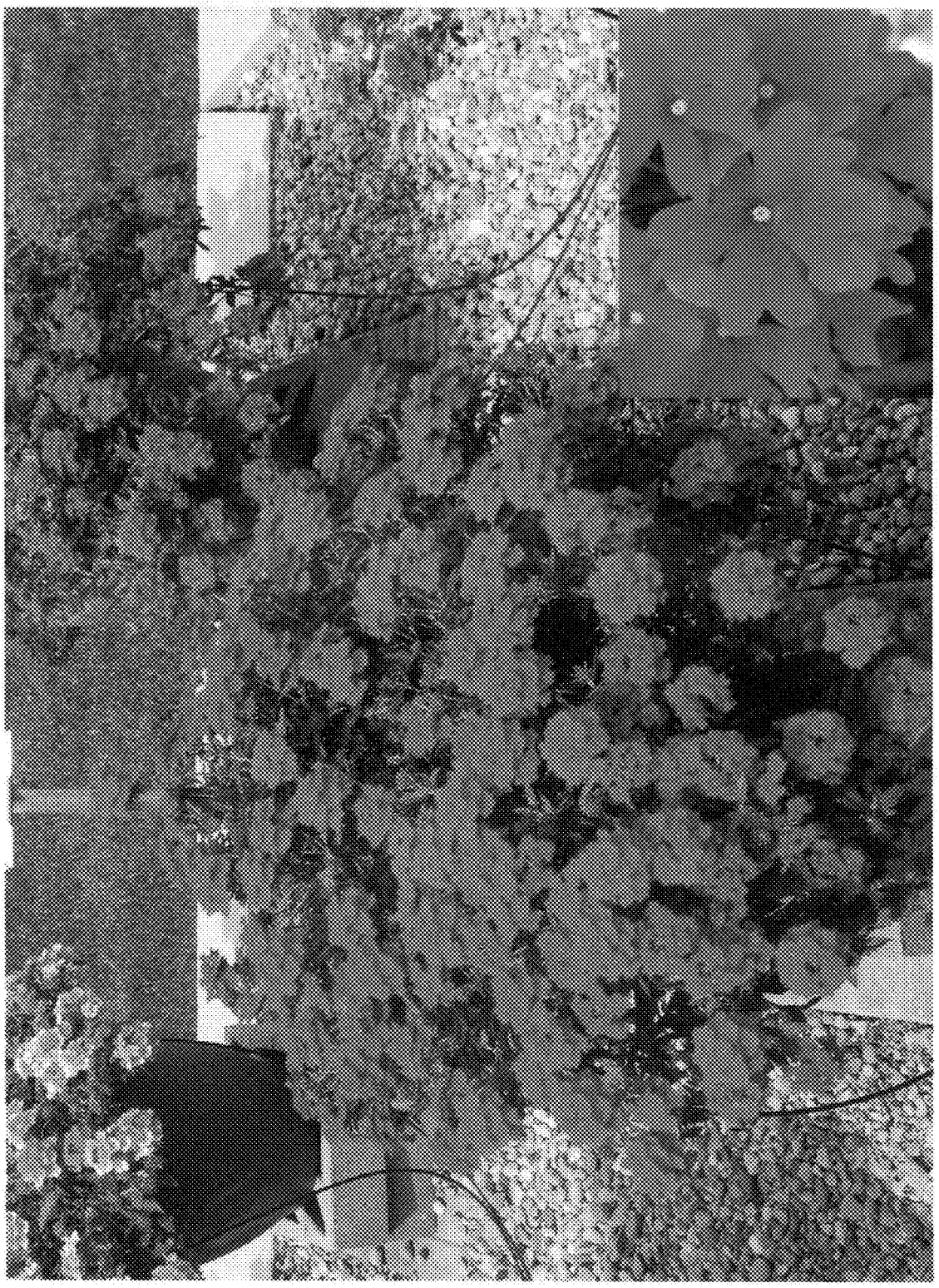

* * * * *